United States Patent [19]  
Schneider

[11] 3,980,724  
[45] Sept. 14, 1976

[54] DIHALOGENATION OF DOUBLY BRANCHED ALKANES

[75] Inventor: Abraham Schneider, Overbrook Hills, Pa.

[73] Assignee: Sun Ventures, Inc., St. Davids, Pa.

[22] Filed: Sept. 10, 1975

[21] Appl. No.: 611,941

Related U.S. Application Data

[63] Continuation-in-part of Ser. No. 129,993, March 31, 1971, abandoned.

[52] U.S. Cl. .......................... 260/658 R; 260/653.8; 260/659 R
[51] Int. Cl.² ......................................... C07C 17/10
[58] Field of Search .......... 260/658 R, 659 R, 653.8

[56] References Cited
UNITED STATES PATENTS

| | | | |
|---|---|---|---|
| 2,831,036 | 4/1958 | Wiese | 260/659 R |
| 3,230,269 | 1/1966 | Mahan et al. | 260/648 R X |
| 3,679,758 | 7/1972 | Schneider | 260/659 R |

Primary Examiner—Daniel E. Wyman  
Assistant Examiner—Thomas A. Waltz  
Attorney, Agent, or Firm—J. Edward Hess; Donald R. Johnson; Stanford M. Back

[57] ABSTRACT

$C_8$–$C_{30}$ alkanes having a chain length of at least 6 carbon atoms and two unbranched $C_1$–$C_3$ alkyl substituents on different carbon atoms separated from each other by 1–3 carbon atoms are dichlorinated, dibrominated or difluorinated by reaction with a $C_4$–$C_5$ tertiary alkyl chloride, bromide or fluoride. The reaction is effected by contacting a mixture of the reactants, containing a large molar excess (>2:1) of the tertiary alkyl halide, with 90–100% sulfuric acid or 90–100% hydrofluoric acid at a temperature below 50°C., preferably 0°–30°C. The dihalide product has a halogen and alkyl substituent at each of two chain carbons which are separated from each other by two other carbon atoms. These dihalides have utility as intermediates for preparing difunctional derivatives, e.g. diacids, dialcohols or diamides, which are useful as monomers in polymer manufacture.

11 Claims, No Drawings

DIHALOGENATION OF DOUBLY BRANCHED ALKANES

CROSS REFERENCES TO RELATED APPLICATIONS

This application is a continuation-in-part of Ser. No. 129,993, filed Mar. 31, 1971, now abandoned.

My copending application Ser. No. 715,958, filed Mar. 26, 1968, now U.S. Pat. No. 3,577,468, issued May 4, 1971, discloses the reaction of alkyladamantanes at −30°C. to 10°C. with $C_4$–$C_5$ tertiary alkyl chlorides, bromides or fluorides, using as catalyst sulfuric acid or hydrofluoric acid of 90–100% strength. The products are essentially monohalo derivatives, although small amounts of dihaloalkyladamantanes may be formed in this reaction.

My copending application Ser. No. 726,132, filed May 2, 1968, now U.S. Pat. No. 3,577,469, issued May 4, 1971, describes the reaction of cis-decahydronaphthalene at −20°C. to 25°C. with $C_4$–$C_5$ tertiary alkyl halides in the presence of sulfuric acid of 90–100% $H_2SO_4$ to yield mainly trans-9-halodecahydronaphthalene. In this reaction the formation of dihalo derivatives is practically negligible.

My copending application Ser. No. 883,579, filed Dec. 9, 1969, now U.S. Pat. No. 3,707,570, issued Dec. 26, 1972, discloses the preparation of dihalo derivatives of alkylcyclohexanes having 1–6 unbranched alkyl substituents on the ring. The procedure involves the use of a $C_4$–$C_5$ tertiary alkyl halide with $AlCl_3$ or $AlBr_3$ as catalyst. This type of catalyst can cause isomerization of alkyl groups on the ring.

My copending application Ser. No. 129,953, filed Mar. 31, 1971, now U.S. Pat. No. 3,763,249, issued Oct. 2, 1973, relates to the dihalogenation of certain alkylcyclohexanes employing the same catalysts (i.e. $H_2SO_4$ or HF) and same reaction conditions as used in the present invention.

BACKGROUND OF THE INVENTION

This invention relates to the conversion of certain alkanes containing two unbranched alkyl groups of the $C_1$–$C_3$ range spaced from each other at specific distances on the chain into dihalogenated derivatives in which the halogen is chlorine, bromine or fluorine. The halogenating agent is a $C_4$–$C_5$ tertiary alkyl chloride, bromide or fluoride. The products are dihalides having a halogen and an alkyl substituent at each of two chain carbons which are separated from each other by two other carbon atoms; for example, 2,5-dichloro-2,5-dichloro-2,5-dimethylhexane. These products have utility as intermediates for preparing difunctional derivatives, e.g., diacids, dialcohols or diamides, which are useful as monomers in polymer manufacture.

Hydrogen-halogen exchange reactions between a tertiary alkyl halide, such as t-butyl chloride, and various hydrocarbons containing one or more tertiary hydrogen atoms, wherein an aluminum chloride catalyst has been used, have been described in the prior art for effecting monohalogenation. Such procedure has been shown, for example, by C. W. Kruse, Preprints, ACS Pet. Div., Vol. 12, No. 2, Advances in Petrochemical Symposium, Miami Beach, Florida (April, 1967), and in the following United States patents:

| PATENTEE | PATENT NO. | ISSUE DATE |
|---|---|---|
| Schmerling | 2,448,156 | Aug. 31, 1948 |
| Condon | 2,629,748 | Feb. 24, 1953 |
| Condon | 2,646,453 | July 21, 1953 |
| Schneider et al. | 2,742,507 | Apr. 17, 1956 |
| Gerzon | 3,096,372 | July 2, 1963 |
| Mahan et al. | 3,230,269 | Jan. 18, 1966 |
| Kruse et al. | 3,247,277 | Apr. 19, 1966 |

However, none of these references teaches the preparation of dihaloalkanes by means of a hydrogen-halogen interchange reaction.

While sulfuric acid generally would be a more desirable catalyst than aluminum chloride for commerical practice, references to its use as a catalyst for hydrogen-halogen exchange reactions are more scarce. The following references on this subject appear to be the most pertinent:

U.S. Pat. No. 2,744,940, issued May 8, 1956, Herman Pines, discloses the monochlorination of various alkylcyclohexanes by means of tertiary butyl chloride and employing strong sulfuric acid as catalyst. Under the reaction conditions taught, monochlorination of the starting naphthene occurs but no dichloro products are produced.

U.S. Pat. No. 2,810,001, issued Oct. 15, 1957, Herbert K. Wiese, discloses the reaction of methylcyclopentane with tertiary butyl chloride at −10° to 25°C. utilizing 85–100% $H_2SO_4$ as catalyst. The patent teaches that monochlorination of the methylcyclopentane at the tertiary carbon atom first occurs but that the monochloro product inevitably further reacts, by undergoing a condensation reaction with liberation of HCl, to produce dicyclic monochloro products.

U.S. Pat. No. 2,831,036, issued Apr. 15, 1958, Herbert K. Wiese, discloses the monochlorination of branched $C_6$–$C_8$ isoparaffins having one or more tertiary carbon atoms by reaction with tertiary butyl chloride at −25° to 25°C. employing 85–100% $H_2SO_4$ as catalyst. The patent gives no indication that dichlorides can be produced in this type of reaction.

SUMMARY OF THE INVENTION

The present invention provides a process for utilizing sulfuric acid or hydrofluoric acid to promote a hydrogen-halogen interchange reaction to convert certain types of alkanes into dihalo derivatives. The starting alkanes have the following characteristics: (1) they are $C_8$–$C_{30}$ alkanes having a chain length of at least six carbon atoms; (2) they have two alkyl substituents which are methyl, ethyl or n-propyl or any combination thereof; and (3) these substituents are attached to different chain carbon atoms which are separated from each other by one, two or three carbon atoms. The procedure involves a hydrogen-halogen interchange reaction between one or more of such alkanes and a $C_4$–$C_5$ tertiary alkyl chloride, bromide or fluoride, promoted by means of sulfuric or hydrofluroic acid having a strength of 90–100%. It is essential that the molar ratio of the halogenating agent to the alkane be at least 2:1. The reaction is carried out at a relatively low temperature, viz. in the range of from the freezing point of the acid phase to 50°C. and more preferably 0°–30°C.

I have now found that doubly branched alkanes, as defined above, having tertiary carbon atoms in the chain separated from each other by 1–3 carbon atoms can be made to undergo hydrogen-halogen exchange reactions at the two tertiary positions by employing either sulfuric or hydrofluoric acid as the catalyst. The resulting dihalogenated product has a halogen and an alkyl substituent at each of two chain carbon atoms which are separated from each other specifically be two carbon atoms. I have further found that alkanes having only one alkyl substituent and those having two alkyl substituents spaced from each other at distances other than as above specified or which have less than six carbon atoms in the chain are essentially incapable of undergoing dihalogenation under these reaction conditions. For example, 2- or 3-methylpentane, or 3-methylheptane or 2-methylheptane will not dihalogenate, nor will 2,2- or 2,4-dimethylpentane or 2,2,3-trimethylhexane yield dihalo derivatives under the conditions employed in the present process.

The process of the invention comprises the following steps:

a. establishing a two-phase admixture of
1. a phase comprising (a) a $C_8$–$C_{30}$ alkane having a chain length of at least 6 carbon atoms and two unbranched alkyl substituents of 1–3 carbon atoms each attached to different chain carbon atoms separated from each other by 1–3 carbon atoms, and (b) a tertiary $C_4$–$C_5$ alkyl halide which is a chloride, bromide or fluoride in a molar ratio to said alkane of at least 2:1,
2. and as a second phase a mineral acid selected from the group consisting of 90–100% sulfuric acid and 90–100% hydrofluoric acid;

B. contacting said phases at a temperature above the freezing point of the acid phase and below 50°C., whereby a hydrogen-halogen interchange reaction between the tertiary alkyl halide and said alkane occurs to form a dihalo derivative;

C. and recovering a dihalide product having a halogen and an alkyl substituent at each of two chain carbons which are separated from each other by two other carbon atoms.

In another embodiment of the invention, monohalides of alkanes as above specified, wherein the halogen (Cl, Br or F) is attached to the chain at a tertiary or secondary position, or mixtures of such tertiary and secondary halides, are converted to dihaloalkanes by contacting a solution thereof in at least an equal molar amount of tertiary $C_4$–$C_5$ alkyl chloride, bromide or fluoride with 90–100% $H_2SO_4$ or 90–100% HF.

DESCRIPTION

As a specific illustration of the process, 10 parts (by weight) of 2-methyl-5-ethyldecane are dissolved in 50 parts of tertiary butyl bromide and the mixture is contacted at 20°C. with 100 ml. of strong sulfuric acid (96% $H_2SO_4$) for 3 hours under a partial pressure of HBr of 50 p.s.i. The acid and organic phases are then separated and the latter is fractionally distilled. A dibrominated product fraction is recovered which consists essentially of 2,5-dibromo-2-methyl-5-ethyldecane. The organic phase also contains monobrominated product which can be separately recovered and recycled for further conversion to the 2,5-dibromo compound.

As a further specific illustration, the invention is utilized to difluorinate 3,6-diethyloctane. A solution of 10 parts (by weight) of the diethyloctane in 40 parts of t-butyl fluoride is formed, and the solution is then contacted with 5 times its volume of anhydrous hydrogen fluoride at 0°C. for 4 hours. The phases are then separated. Water washing followed by fractional distillation of the organic phase yields a fraction composed of 3,6-difluoro-3,6-diethyloctane. A monofluoride derivative, which is at least mainly the tertiary monofluoride of 3,6-diethyloctane, can also be recovered and reacted in analogous manner for further conversion to the 3,6-difluoro product.

The halogenating agent employed is a $C_4$ or $C_5$ tertiary alkyl chloride, bromide or fluoride or, in other words, t-butyl or t-amyl chloride, bromide or fluoride. Mixtures of these halogenating agents can be used, although it is generally preferable to use a single halogenating agent and usually t-butyl chloride is preferred. Primary or secondary halides are not suitable, for these are largely inert under the reaction conditions of the present process. The molar ratio of halogenating agent to the alkane in the feed mixture is important and must be at least 2:1, as otherwise good yields of the desired dihalide product cannot be secured. Preferably the molar ratio of the alkyl halide agent to the alkane reactant is above 3:1 and much larger ratios, e.g. 6:1 or 10:1, can be used if desired. After the reaction is completed, any unreacted halogenating agent can be recovered and recycled.

The catalyst for the present reaction can be either strong sulfuric acid or strong hydrofluoric acid. When an alkyl chloride or bromide is used as the halogenating agent, it is preferably to use sulfuric acid rather than hydrofluoric acid as the catalyst. This avoids the possibility of halogen-halogen interchange that otherwise might occur between the HF and the alkyl chloride or bromide or the chloro or bromo reaction product. Such interchange could result in mixed dihalo derivatives of the alkane which ordinarily would not be desired as the product. On the other hand, when an alkyl fluoride is used as the halogenating agent, halogen-halogen interchange is not a factor and either HG or $H_2SO_4$ can advantageously be employed.

The strength of the acid should be in the range of, by weight, 90–100% $H_2SO_4$ or 90–100% HF. Preferably sulfuric acid with a strength of 95–99% $H_2SO_4$ is used. When hydrofluoric acid is employed, a strength in the range of 94–100% HF is preferred. Strength as here used is calculated on an organic matter-free basis and relates to the proportion of $H_2SO_4$ or HF to water present. The catalyst constitutes a liquid phase separate from the organic phase, and the rate of conversion depends upon the intimacy of contacting the two phases. Good agitation expedites conversion and an increase in the ratio of the acid phase to the organic phase also increases the rate of conversion. Usually a volume ratio of acid to organic phase in the range of 1:2 to 20:1 is employed and a ratio in the range of 2:1 10:1 is preferred.

When sulfuric acid is used as the catalyst, it is advantageous to conduct the reaction under a partial pressure of HCl, HBr or HF, e.g. a partial pressure in the range of 10–100 p.s.i. The presence of the hydrogen halide tends to inhibit side reactions and helps to secure a higher conversion of the starting alkane to the dihalo derivative. Preferably the hydrogen halide employed for this purpose has the same kind of halogen as the tertiary alkyl halide used, so as to avoid the possibility of transhalogenation resulting in different halogen substituents in the reaction products. However such identity of the halides present is not essential for operability of the process, and alkylating agents and hydrogen halides having different halogens can be used together if desired.

The temperature for carrying out the reaction is relatively low, i.e. in the range of from the freezing point of the acid phase to 50°C. Higher temperatures should be avoided since undesirable side reactions will occur. Preferably a reaction temperature in the range of 0° to 30°C. is employed. The acid and organic phases are contacted at a temperature in the specified range until at least a substantial yield of the dihaloalkane product has been obtained. Suitable reaction times usually are in the range of 0.5–24 hours.

The hydrocarbon feed can be one or more alkanes having precisely two unbranched alkyl groups of the $C_1$–$C_3$ range attached to tertiary carbon atoms in the chain which are spaced apart via 1–3 intermediate carbon atoms. In other words, these two substituents can be methyl, ethyl or n-propyl, or any combination of these alkyl groups, and are attached to the chain at different carbon atoms which have one, two or three carbon atoms between them. For example, if one of the alkyl substituents is located at the 2-position, then the other alkyl group must be situated at the 4-, 5- or 6-position, preferably the 5-position. Any alkanes as here defined can be dichlorinated, dibrominated or difluorinated in the present process. The resulting dihalogenated product will have the halogen atoms attached to carbon atoms which are spaced apart by precisely two intervening carbon atoms in the chain and further will have the alkyl groups attached to the same carbon atoms as the halogen substituents.

The following equation illustrates the desired reaction, starting with 2,5-dimethylhexane and t-butyl chloride (most hydrogen atoms being omitted, for convenience):

or 2,6-positions or when the alkyl groups are located with these spacings at other positions along the chain, formation of the dihalo derivative generally entails isomerization of one or both alkyl groups to positions at which the two tertiary carbon atoms are separated by two intermediate carbon atoms. Thus essentially no dihalogenated product is obtained until the skeletal structure of the reactant has rearranged to give this spacing between the two tertiary carbon atoms. The ability to dihalogenate evidently depends upon anchimeric assistance [see Winstein et al., JACS, 75, 147 (1953)] which results mostly from this spacing of the first halogen substituent from the second tertiary hydrogen atom.

When the reaction has been completed, the acid phase is separated from the organic phase and the latter may be washed with water to remove any traces of acid remaining. The dihalogenated product can then be separated from the other components in any suitable manner, for example, by fractional crystallization of distillation.

The dihaloalkanes produced by the present invention are useful as intermediates for preparing monomers suitable for making various types of polymers such as polyesters or polyamides. For example, the dihaloalkanes can be reacted in the presence of strong sulfuric acid with formic acid [see Koch et al., Liebig's Annalen der. Chemie, 618, 251–266 (1958)] to produce corresponding diacids, or with HCN or nitriles [analogous to Ritter reaction, JACS, 70, 4045–4048 (1948)] to form corresponding diamides. Dialcohols, also useful as monomers, can be made by esterifying the diacids and hydrogenating the resulting diesters. Such diacids and dialcohols can be used, for example, to make copolymers analogous to those shown in Caldwell et al. U.S. Pat. No. 2,891,930, issued June 23, 1959, which de-

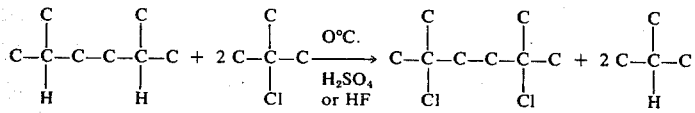

The products of the reaction, as shown, are 2,5-dichloro-2,5-dimethylhexane and isobutane. This dichloro compound is the only dichloride derivative of the feed hydrocarbon that is obtained in the reaction. During the reaction the hydrocarbon is first converted to its tertiary monochloride (not shown). Continuing the contacting of phases causes the tertiary monochloride to convert to the ditertiary-dichloride, viz. the 2,5-dichloride, which is the only dichloride derivative obtained. Generally the reaction mixture, after phase contacting has been stopped, will contain a considerable amount of the tertiary monochloride and may contain a small amount of secondary monochloride in addition to the desired 2,5-dichloro product. The monochloride product usually will exceed the dichloride in amount in view of the difficulty in achieving dihalogenation of the alkane via hydrogen-halogen transfer. The monochloride can be separated by distillation from the dichloride product and recycled or treated separately for further conversion to 2,5-dichloro-2,5-dimethylhexane.

Other doubly branched alkanes, as herein specified, undergo halogenation in the present process in a manner analogous to that described above for 2,5-dimethylhexane. However, when the alkyl substituents have 2,4- scribes the use of 1,4-cyclohexanedicarboxylic acid and various diols for preparing polyesters.

The dihalo product, 2,5-dihalo-2,5-dimethylhexane, which can be made from 2,4- or 2,5-dimethylhexane by the present invention, is a useful intermediate in the preparation of p-xylene, since it can be dehydrohalogenated to give the diolefin, 2,5-dimethylhexadiene-2,4, which can be dehydrocyclized by means of a chromia-alumina catalyst to yield p-yxlene.

The examples below are specific illustrations of reactions under conditions of the invention. In all runs the organic phases separated from the reaction mixtures were analyzed by GLC.

EXAMPLE I

This run illustrates the dichlorination of 2,5-dimethylhexane (DMH). The reaction mixture was composed of 10 ml. of 96% $H_2SO_4$, 1.05 g. (0.0096 mole) of 2,5-DMH and 2.18 g. (0.0235 mole) of t-butyl chloride. The molar ratio of t-butyl chloride to the DMH was 2.6. These materials were charged to a shaker bomb, gaseous HCl was admitted therein to a partial pressure of 83 p.s.i., and the mixture was shaken for 3 hours at 20°C. Analysis of the organic phase gave the results shown in Table I, which shows the charge composition and the total composition of the final organic layer.

EXAMPLE II

Another run was made like the preceding example using the same reactants, but the molar ratio of t-butyl chloride to 2,5-DMH was increased from 2.6 to 5.2. Specifically the reaction mixture contained 10 ml. of 96% $H_2SO_4$, 0.50 g. (0.0045 mole) of 2,5-DMH and 2.0 g. (0.0227 mole) of t-butyl chloride. A partial pressure of HCl of 88 p.s.i. was used, and the mixture was shaken for 3 hours at 20°C. Results are also given in Table I.

TABLE I

Reaction of 2,5-Dimethylhexane (DMH)
Composition, area %

| Components | Example I Original | Example I After 3 Hrs. | Example II Original | Example II After 3 Hrs. |
|---|---|---|---|---|
| isobutane | — | 8.4 | — | 5.6 |
| t-butyl chloride | 66.1 | 40.6 | 82.4 | 62.8 |
| amyl chlorides* | — | 1.8 | — | 2.0 |
| 2,5-DMH | 33.9 | 10.4 | 17.6 | 3.2 |
| hexyl chlorides* | — | 1.9 | — | 1.6 |
| heptyl chlorides* | — | 0.5 | — | 0.1 |
| 2-chloro-2,5-DMH | — | 25.0 | — | 13.6 |
| trimethylpentyl chlorides* | — | 2.2 | — | 2.0 |
| 2,5-dichloro-2,5-DMH | — | 8.3 | — | 9.1 |
| higher boiling chlorides* | — | 0.9 | — | trace |

*mixture of compounds

The data in Table I show substantial formation of the 2,5-dichloro derivative of the starting hydrocarbon and that this was the only dichloride produced therefrom. The small amounts of amyl, hexyl, heptyl and trimethylpentyl chlorides and the higher boiling chlorides evidently result from reactions of the t-butyl chloride such as disproportionation and polymerization. Calculations of yields of materials derived from the hydrocarbon feed, based on 2,5-DMH charged, are shown in Table II for the two runs.

TABLE II

| | Yield, % Example I | Yield, % Example II |
|---|---|---|
| 2,5-DMH (unconverted) | 30 | 18 |
| 2-chloro-2,5-DMH | 55 | 53 |
| 2,5-dichloro-2,5-DMH | 15 | 29 |

The unconverted DMH and the monochloride product shown for each of these runs could be recovered and recycled for further conversion to 2,5-dichloro-2,5-DMH under similar reaction conditions.

EXAMPLE III

In another run using 2,5-DMH under conditions much like those used in Example I except that no HCl was added to the reaction zone, it was found that the reaction mixture after 3 hours time at 0°C. contained a considerably higher proportion of the chloride by-products derived from the t-butyl chloride relative to the desired 2,5-dichloro product than was the case in Example I. This shows that the use of a partial pressure of HCl in the reaction zone tends to suppress side reactions.

EXAMPLE IV

In this example the feed reactant was 2,6-dimethylheptane (DMHp). The reaction mixture was composed of 10 ml. of 96% $H_2SO_4$, 1.0 g. (0.0078 mole) of 2,6-DMHp and 1.44 g. (0.0317 mole) of t-butyl choride. The molar ratio of t-butyl chloride to DMHp was 2.0, and no HCl was added. The mixture was shaken at 0°C. and samples of the organic phase at total reaction times of 30, 60 and 140 minutes, respectively, were taken and analyzed by GLC. Results of the analyses are shown in Table III.

TABLE III

Reaction of 2,6-Dimethylheptane (DMHp)

| | Charge | Cut 1 | Cut 2 | Cut 3 |
|---|---|---|---|---|
| Total reaction time, min. | 0 | 30 | 60 | 140 |
| Composition, area %: | | | | |
| isobutane | — | 1.6 | 3.6 | 6.2 |
| t-butyl chloride | 60.8 | 43.9 | 37.2 | 29.0 |
| amyl chlorides* | — | 2.6 | 3.3 | 4.9 |
| hexyl chlorides* | — | 1.9 | 2.9 | 3.9 |
| 2,6-DMHp | 39.2 | 40.3 | 37.7 | 35.2 |
| heptyl chlorides* | — | 0.2 | 0.5 | 0.5 |
| 2-chloro-2,5-dimethylhexane | — | 0.8 | 1.3 | 1.7 |
| trimethylpentyl chlorides* | — | 2.5 | 2.8 | 2.8 |
| 2-chloro-2,6-DMHp | — | 2.4 | 4.6 | 7.3 |
| 2,5-dichloro-2,5-dimethyl-hexane | — | 0.7 | 1.0 | 1.2 |
| 2,5-dichloro-2,5-DMHp | — | 0.9 | 2.2 | 2.8 |
| higher boiling chlorides* | — | 2.4 | 2.8 | 4.5 |

*mixture of compounds

The results in Table III show that the 2,6-dimethylhexane undergoes reaction quite slowly under the conditions of this run but nevertheless that the dichlorination reaction does proceed to give 2,5-dichloro-2,5-DMHp. This entails the isomerization of a methyl to give the 2,5-spacing that provides anchimeric assistance for dihalogenation. The data also show that an appreciable amount of the $C_8$ dichloro product, 2,5-dichloro-2,5-dimethylhexane, was produced.

EXAMPLES V-VII

Three runs were made in a manner similar to preceding examples but using 2,4-dimethylhexane (DMH) as the feed hydrocarbon. Molar ratios of t-butyl chloride to this hydrocarbon were in the range of 2.0 to 2.6. Other conditions are shown in Table IV, which also gives product yields calculated from the analyses of samples taken at various reaction times. For this hydrocarbon feed the monochloride material which formed included tertiary monochlorides of 2,4-DMH as well as 2-chloro-2,5-DMH, and the yields of these are shown separately in Table IV. The only dichloride formed was 2,5-dichloro-2,5-DMH.

TABLE IV

Reactions of 2,4-Dimethylhexane

| Example | HCl Pressure, p.s.i. | Temp., 0°C. | Total Reaction Time, min. | Feed Unconverted | 2-chloro-2,5-DMH | Monochlorides of 2,4-DMH | 2,5-dichloro-2,5-DMH |
|---|---|---|---|---|---|---|---|
| V | 0 | 0 | 60 | 89.6 | 6.9 | 2.0 | 1.5 |
|   |   |   | 180 | 81.5 | 17.7 | 6.7 | 4.1 |
| VI | 40 | 10 | 180 | 56.3 | 26.8 | 10.9 | 6.0 |
| VII | 83 | 20 | 180 | 57.4 | 27.8 | 8.3 | 6.5 |

Yield, mole % on feed

The results given in Table IV indicated that 2,4-DMH at the reaction conditions employed slowly converts to the single dichloride, 2,5-dichloro-2,5-dimethylhexane.

Analogous results are obtained when other doubly branched alkanes as herein specified are substituted for the feed hydrocarbons used in Examples I-VII. Likewise essentially equivalent results are obtained when tertiary butyl bromide or fluoride is used in place of the tertiary chloride. The halogenation reaction also proceeds in essentially the same manner when tertiary amyl chlorides, bromides or fluorides are used, but in such cases more side reactions tend to occur. The use of HF in place of $H_2SO_4$ gives similar results, except that when HF is used in combination with a tertiary $C_4$–$C_5$ alkyl chloride or bromide, reactions involving halogen-halogen interchange may also take place resulting in products having mixed halogen substituents.

EXAMPLE VIII

This example shows the critical nature of the specified structure of the starting material. This example is a run essentially the same as the procedure described in Wiese, U.S. Pat. No. 2,831,036 mentioned previously. A solution of 0.0141 mole of 2,4-dimethylpentane and 0.0293 mole of t-butyl chloride was shaken with 10 ml of 96% $H_2SO_4$ at 0°C in a sealed bottle. The mole ratio of the t-butyl chloride to dimethylpentane was 2:1. After 5, 25, 71.2 and 195 minutes reaction the hydrocarbon phase was sampled (Cuts 1, 2, 3 and 4, respectively) and analyzed. Cuts 1, 2, 3 and 4 showed an orderly increase in the amount of $C_7$ monochlorides but no trace of $C_7$ dichloride was found in any cut.

Another embodiment of the invention comprises converting monohaloalkanes, corresponding to the alkane feed hydrocarbons above specified, into the same dihaloalkane products as would be obtained when the hydrocarbon feed is used. The monohalo feed material in this embodiment can have a chlorine, bromine or fluorine substituent attached at a tertiary or secondary position in the chain of the alkyl moiety. This feed can be the monohalides normally recovered as intermediate reaction products in reacting the alkanes as previously described or it can be monohaloalkanes having the specified structural characteristics and obtained in any other suitable manner, e.g. by addition of HCl, HBr or HF to alkenes corresponding structurally to the described alkane feed materials. In this embodiment the monohaloalkane is dissolved in at least an equimolar part and preferably in at least two parts of the $C_4$–$C_5$ tertiary alkyl chloride, bromide or fluoride and the mixture is contacted with 90–100% sulfuric acid or 90–100% hydrofluoric acid under the same conditions as employed in reacting the hydrocarbon feed. Preferably the type of halogen in both reactants is the same, although this is not essential. This converts the monohalide into the corresponding dihaloalkane. For example, in this manner a mixture of tertiary and secondary monochloro-2,5-dimethylhexane is converted to 2,5-dichloro-2,5-dimethylhexane as the sole dichloride product.

When monohalides are recovered in addition to the desired dihalide product after reacting an alkane feed, they can be reacted separately as above described for further conversion to dihalides, or they can be recycled for further conversion in admixture with more alkane feed. In the latter case the amount of $C_4$–$C_5$ tertiary alkyl halide used should be at least 2 moles per mole of alkane present plus at least one mole per mole of monohalide recycled. Preferably molar ratios substantially above these proportions are used, such as at least 3:1 and at least 2:1, respectively.

What is claimed is:
1. Process of preparing dihalogenated alkanes which comprises:
   A. establishing a two-phase admixture of
      1. a phase comprising (a) a $C_8$–$C_{30}$ alkane having a chain length of at least 6 carbon atoms and two unbranched alkyl substituents of 1–3 carbon atoms each attached to different chain carbon atoms separated from each other by 1–3 carbon atoms, and (b) a tertiary $C_4$–$C_5$ alkyl halide which is chloride, bromide or fluoride in a molar ratio to said alkane of at least 2:1,
      2. and as a second phase 90–100% sulfuric acid;
   B. contacting said phases at a temperature above the freezing point of the acid phase and below 50°C., whereby a hydrogen-halogen interchange reaction between the tertiary alkyl halide and said alkane occurs to form a dihalo derivative;
   C. and recovering a dihalide product having halogen and an alkyl substituent at each of two chain carbons which are separated from each other by two other carbon atoms.

2. Process according to claim 1 wherein the molar ratio of said alkyl halide to said alkane is above 3:1.

3. Process according to claim 2 wherein the strength of the sulfuric acid is 95–99% $H_2SO_4$.

4. Process according to claim 3 wherein said halide is tertiary butyl chloride.

5. Process according to claim 4 wherein said temperature of contacting is in the range of 0°–30°C.

6. Process according to claim 1 wherein said alkane has two methyl substituents.

7. Process according to claim 1 wherein said tertiary $C_4$–$C_5$ alkyl halide is a chloride and its molar ratio to the alkane is above 3:1.

8. Process according to claim 7 wherein said alkyl halide is tertiary butyl chloride, the strength of the sulfuric acid if 95–99% $H_2SO_4$ and said temperature of contacting is in the range of 0°–30°C.

9. Process according to claim 8 wherein said alkane is 2,4-dimethylhexane or 2,5-dimethylhexane and 2,5-dichloro-2,5-dimethylhexane is recovered from the reaction mixture.

10. Process according to claim 9 wherein said alkane is 2,5-dimethylhexane.

11. Process according to claim 1 wherein monohalide product of the starting alkane is also recovered from the reaction mixture and the monohalide product is recycled for further reaction in step (B) in admixture with said alkane.

* * * * *